US00PP24895P2

(12) United States Plant Patent
Miskovsky

(10) Patent No.: US PP24,895 P2
(45) Date of Patent: Sep. 16, 2014

(54) ***PANICUM* PLANT NAMED 'CAPE BREEZE'**

(50) Latin Name: *Panicum virgatum*
Varietal Denomination: Cape Breeze

(71) Applicant: Paul Miskovsky, Falmouth, MA (US)

(72) Inventor: Paul Miskovsky, Falmouth, MA (US)

(73) Assignee: North Creek Nurseries, Inc., Landenberg, PA (US)

( * ) Notice: Subject to any disclaimer, the term of this patent is extended or adjusted under 35 U.S.C. 154(b) by 0 days.

(21) Appl. No.: 13/986,167

(22) Filed: Apr. 8, 2013

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of Panicum virgatum, 'Cape Breeze', that is characterized by its foliage that is deep green in color in summer and turns green with purple-red tips in the fall with foliage coloration retained late in the growing season, its early blooming habit, its inflorescence that are golden tan in color, its compact plant habit, and its good resistance to *Puccinia emaculata* rust.

2 Drawing Sheets

Botanical classification: *Panicum virgatum.*
Varietal denomination: 'Cape Breeze'.

BACKGROUND OF THE INVENTION

The present invention relates to a new and distinct cultivar of *Panicum virgatum* of hybrid origin and will be referred to hereafter by its cultivar name, 'Cape Breeze'. 'Cape Breeze' represents a new cultivar of switchgrass, an ornamental grass grown for landscape use.

The Inventor discovered the new cultivar, 'Cape Breeze', as naturally occurring whole plant mutation in a garden in Oak Bluffs, Martha's Vineyard, Mass. in 2008. The parent plants are unknown and the Inventor believes that the new cultivar is most likely a hybrid of *Panicum virgatum* and another unidentified species of *Panicum.*

Asexual propagation of the new cultivar was first accomplished by division by the Inventor in Oak Bluffs, Martha's Vineyard, Mass. in April 2012. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Cape Breeze' as a unique cultivar of *Panicum virgatum.*

1. 'Cape Breeze' exhibits foliage that is deep green in color in summer and turns green with purple-red tips in the fall with foliage coloration retained late in the growing season.
2. 'Cape Breeze' is early blooming; blooming earlier than in typical of plants of *Panicum virgatum.*
3. 'Cape Breeze' inflorescences that are golden tan in color.
4. 'Cape Breeze' has a compact plant habit; reaching about 24-30 inches in height and spread.
5. 'Cape Breeze' exhibits good resistance to rust.

'Cape Breeze' can be most closely compared to cultivars, 'Warrior' (not patented), and 'Huron Solstice' (U.S. Plant Pat. No. 21,498). 'Warrior' differs from 'Cape Breeze' in having a much taller plant habit, less resistance to rust, and darker colored inflorescences. 'Huron Solstice' differs from 'Cape Breeze' in having foliage that is lighter green in color with the color not retained as late in the season, in having much less rust resistance, in having a taller and less compact plant habit.

BRIEF DESCRIPTION OF THE DRAWINGS

The accompanying photographs were taken in October and illustrate the characteristics of 2 year-old plants as grown outdoors in a trial garden in Oak Bluffs, Martha's Vineyard, Mass.

The photograph in FIG. 1 depicts the plant habit and foliage coloration of 'Cape Breeze' in fall.

Figure 1:
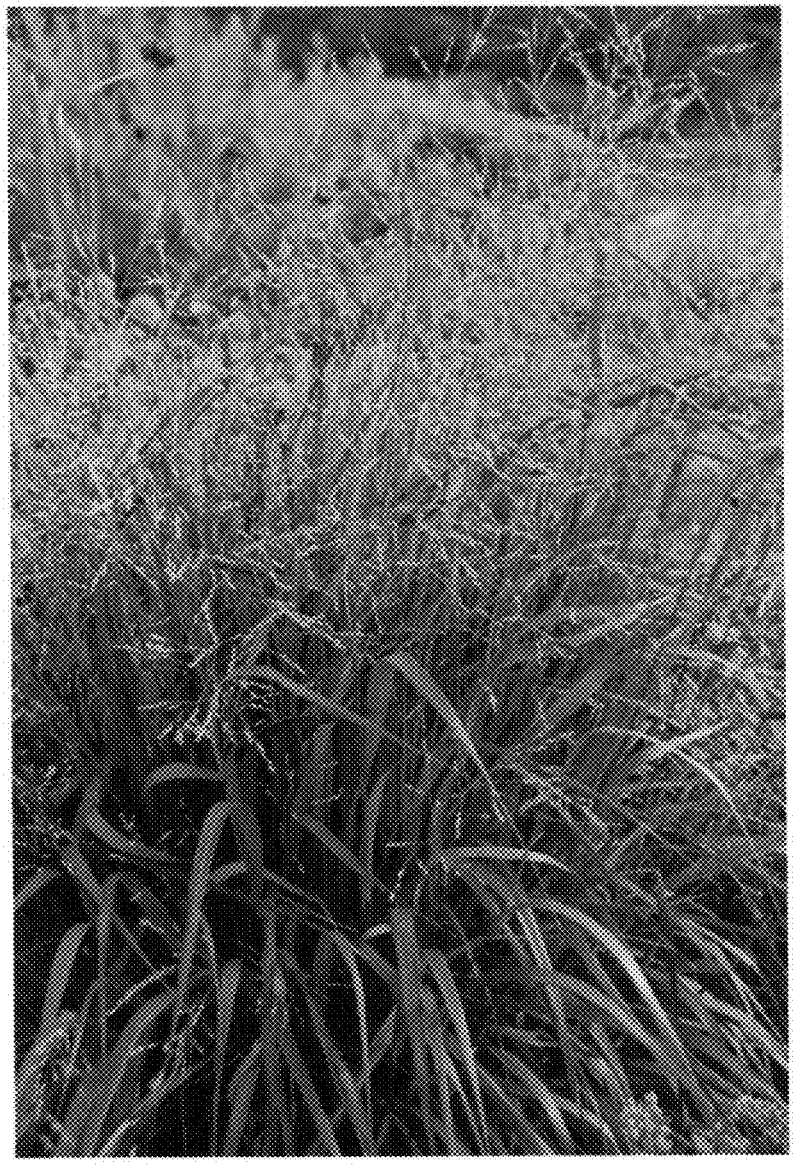
Figure 2:
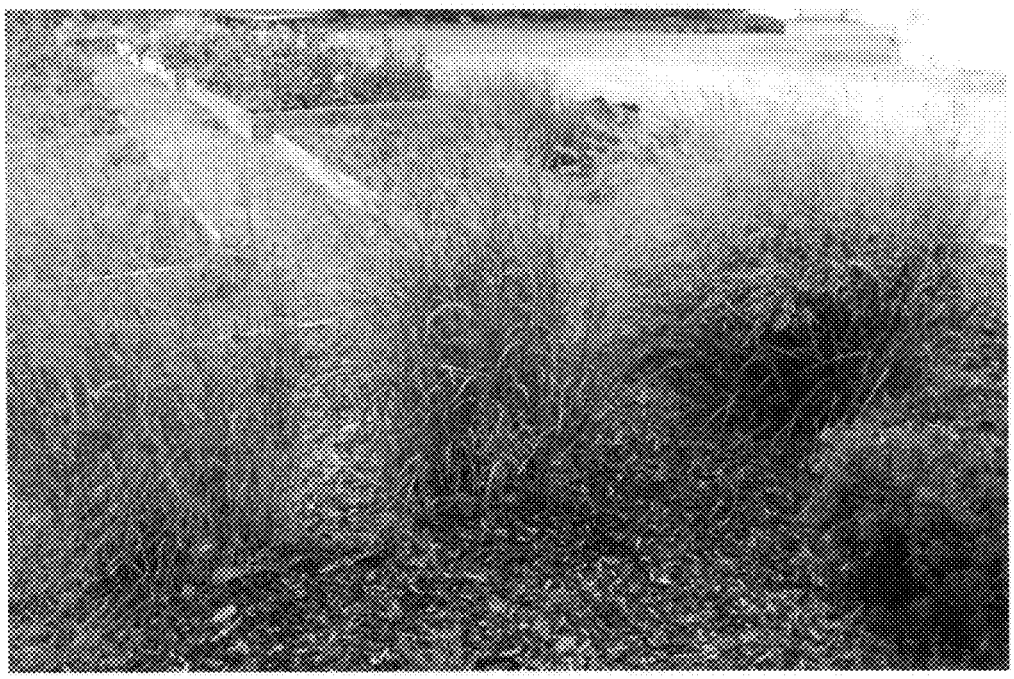

The photograph in FIG. 2 provides a comparison between plants of *Panicum virgatum* 'Warrior' (plant in the middle), *Panicum virgatum* 'Huron Solstice' (plant on left) and 'Cape Breeze' (plant on right), with the color retention of the foliage of 'Cape Breeze' in fall illustrated.

The colors in the photograph may differ slightly from the color values cited in the detailed botanical description, which accurately describe the colors of the new *Panicum virgatum.*

DETAILED BOTANICAL DESCRIPTION

The following is a detailed description of one-year-old plants of the new cultivar as grown in two-gallon containers in Landenberg, Pa. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early blooming; from late spring to fall in city, Martha's Vineyard, Mass.

*Plant type.*—Herbaceous perennial grass.

*Plant habit.*—Compact, upright mound.

*Height and width or spread.*—Reached about 24-30 inches in height and spread.

*Hardiness zone.*—At least in U.S.D.A. Zones 5 to 8.

*Diseases and pests.*—Has shown good resistance to *Puccinia emaculata* rust.

*Root description.*—Fibrous, deep rooted.

*Propagation.*—Culm division and tissue culture (preferred).

*Growth rate.*—Moderate.

Culm (stem) description:

*General.*—Cylindrical, hollow pith, thin but strong, erect.

*Culm number.*—25 in a 2-gallon container, forming tight clump.

*Culm color.*—137B in summer, 175C in fall, 161D and 158A in winter, ranges from 2 to 10 cm of exposed area between leaf nodes.

*Culm size.*—Average of 2 mm in diameter, averaging 36 cm in height from the base to the tip of the flower panicle.

*Culm surface.*—Glabrous.

*Internode length.*—An average of 7 cm.

Foliage description:

*Leaf shape.*—Narrowly lanceolate.

*Leaf division.*—Simple.

*Leaf margin.*—Entire, slightly scabrous.

*Leaf base.*—Sheathed to base of the node.

*Leaf venation.*—Parallel, not distinguishable in color from leaf.

*Leaf width.*—Average of 1.2 cm at widest section.

*Leaf length.*—Blade; an average of 232 cm, sheathed portion; an average of 7 cm.

*Leaves per culm.*—Average of 4.

*Leaf surface.*—Glabrous and dull on both surfaces.

*Ligule.*—1.5 mm in width, hairy on inner surface, 144D in color.

*Leaf color (both surfaces).*—Summer; N137A, fall; N137A with 187A to 187B tips with the coloration retained into late fall, winter; 161D.

Flower description:

*Inflorescence type.*—Airy panicle at terminus of stem, symmetrical, typically 2-flowered spikelet with lower flower male and upper flower hermaphrodite, overall color of the raceme is 145B in early summer and maturing to 161D in late fall.

*Inflorescence size.*—Average of 23 cm in length and 6 cm in width.

*Spikelet description.*—Average of 180 per panicle, awnless, lower glume 1.5 mm in length and 1.5 mm in width, upper glume and lower lemma extending about 2.5 cm in length and width, glumes and lower lemma are convex with both surfaces glabrous surface and 144D in color with thin stripes of 137B, upper lemma is translucent, an average of 1.5 mm in length and width, and 144D in color.

*Spikelet size.*—About 3 mm in length and 2 mm in width.

*Rachis.*—An average of 30 from last leaf, raceme portion an average of 20 cm in length, 2 mm at base and 0.2 mm at apex in width, glabrous surface, 137B in color, lateral branches (peduncle-like); an average of 15, 0.2 mm in width and an average of 5.5 cm in length (shortest at terminus), 137B in color, glabrous surface, on spikelet (pedicel like); an average of 5 mm in length, wiry, 137B in color, glabrous surface.

Reproductive organs:

*Androecium.*—Anthers; 3, 1 mm in length and 0.5 mm in width, 165A in color, basifixed on very fine filament, Pollen; moderate in quantity, 164B in color.

*Gynoecium.*—Pistil; 1, 2 plumose stigmas on short, file styles, stigma color is 75A, 1.5 mm in length and 1 mm in width, ovary; 1-locular, superior, 1 mm in length, 144D in color.

*Caryopsis.*—2 to 3 mm in length and about 1.5 in width, 165C in color.

It is claimed:

1. A new and distinct cultivar of *Panicum virgatum* plant named 'Cape Breeze' as herein illustrated and described.

* * * * *